(12) United States Patent
Gruen et al.

(10) Patent No.: US 8,597,569 B2
(45) Date of Patent: Dec. 3, 2013

(54) SELF-STERILIZING USER INPUT DEVICE

(75) Inventors: Robert Warren Gruen, Kirkland, WA (US); James F. St. George, Seattle, WA (US)

(73) Assignee: Microsoft Corporation, LLC, Redmond, WA (US)

( * ) Notice: Subject to any disclaimer, the term of this patent is extended or adjusted under 35 U.S.C. 154(b) by 484 days.

(21) Appl. No.: 12/762,385

(22) Filed: Apr. 19, 2010

(65) Prior Publication Data
US 2011/0256019 A1 Oct. 20, 2011

(51) Int. Cl.
*G06F 3/041* (2006.01)

(52) U.S. Cl.
USPC ............... 422/24; 422/3; 422/22; 345/173; 345/174; 345/175; 345/176; 345/177; 345/178; 250/461.1; 250/453.11; 250/454.11; 250/455.11

(58) Field of Classification Search
USPC ........ 422/3, 22, 24; 345/173–178; 250/461.1, 250/453.11, 454.11, 455.11
See application file for complete search history.

(56) References Cited

U.S. PATENT DOCUMENTS

| 4,703,572 | A | 11/1987 | Chapin |
| 4,728,936 | A * | 3/1988 | Guscott et al. ............... 340/525 |
| 6,458,331 | B1 | 10/2002 | Roberts |
| 6,752,946 | B2 | 6/2004 | Toyooka |
| 7,394,058 | B2 | 7/2008 | Chua et al. |
| 2004/0036405 | A1 | 2/2004 | Hwang |
| 2006/0188389 | A1 * | 8/2006 | Levy ............................. 422/24 |
| 2007/0026089 | A1 | 2/2007 | Hu |
| 2007/0195550 | A1 * | 8/2007 | Tsai ............................. 362/600 |
| 2007/0196235 | A1 * | 8/2007 | Shur et al. ..................... 422/62 |
| 2007/0205382 | A1 * | 9/2007 | Gaska et al. ............. 250/504 R |
| 2007/0258852 | A1 * | 11/2007 | Hootsmans et al. ............ 422/24 |
| 2008/0067417 | A1 * | 3/2008 | Lane et al. ............... 250/455.11 |
| 2009/0080215 | A1 | 3/2009 | Anandan |

OTHER PUBLICATIONS

"Sharp to Incorporate UV2A*1 Technology into Production of LCD Panels", Retrieved at <<http://sharp-world.com/corporate/news/090916.html>>, Sharp, Sep. 16, 2009, pp. 1-4.
Huang, et al., "68.3: Dual-Sided Slim LCD Display System with UV Excited Flat Backlight", Retrieved at << http://www.kismart.com.tw/download/SID_68-3.pdf >>, 2009, pp. 4.

* cited by examiner

*Primary Examiner* — Brian R Gordon
*Assistant Examiner* — Shogo Sasaki
(74) *Attorney, Agent, or Firm* — Hope Baldauff, LLC

(57) ABSTRACT

Technologies are described herein for providing sterilization of a touchscreen or other tactile input surface of a user input device. A self-sterilizing user input device includes a touchscreen for receiving tactile user input and an ultraviolet (UV) light source that emits UV light onto a touchscreen at a sterilization wavelength. A controller selectively activates and deactivates the UV light source according to whether a user is at or near the user input device. According to one aspect, the user input device includes a backlight to illuminate the touchscreen. The UV light source is positioned with the backlight to provide the UV light from a rear side of the touchscreen.

13 Claims, 5 Drawing Sheets

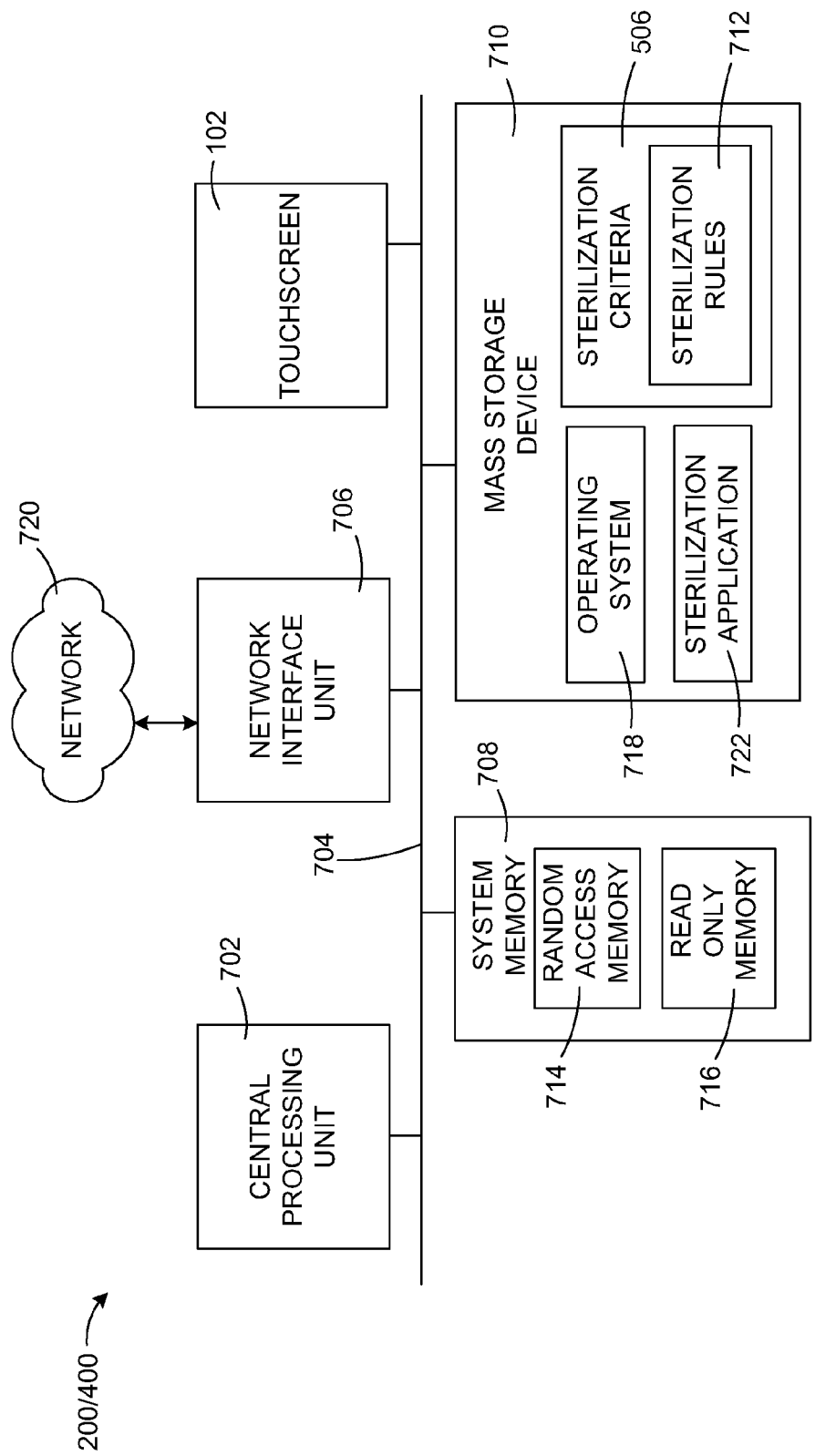

US 8,597,569 B2

SELF-STERILIZING USER INPUT DEVICE

BACKGROUND

As technology advances, people spend an increasing amount of time interacting with electronic devices. For example, people are increasingly utilizing automated teller machines (ATMs) for all of their banking needs, utilizing self-checkout kiosks at grocery and other retail stores, utilizing kiosks at the airport for checking in and printing boarding passes for flights, and utilizing smart phones and tablet computing devices for not only communication purposes, but also to take advantage of an almost limitless number of applications executing on the device. Smart phones and tablet computing devices, in particular, are often shared between friends and family members while playing games and while taking and viewing pictures.

Many of these electronic devices use touchscreen technology to receive user input. Due to the considerable quantities of people that interact with any given touchscreen in a single day, the potential for spreading germs and disease from person to person is significant. Even if a touchscreen associated with a public kiosk was cleaned on a daily basis, there could be hundreds, if not thousands, of people interacting with the device between cleanings, creating a significant gateway to transmitting illness.

It is with respect to these considerations and others that the disclosure made herein is presented.

SUMMARY

Technologies are described herein for sanitizing a touchscreen on a user input device utilizing controlled emissions of ultraviolet (UV) backlight. According to one aspect presented herein, a self-sterilizing user input device includes a touchscreen that receives tactile input from a user. A UV light source emits UV light onto the touchscreen at a sterilization wavelength. The device further includes a controller that selectively activates and deactivates the UV light source according to whether or not a user is present.

According to other aspects, a method of sterilizing a user input device includes determining that a user is not within a certain distance to the user input device. In response to determining that the user is not close, UV light is emitted from a UV light source of the device. This UV light is emitted onto a touchscreen of the device at a sterilization wavelength. A determination is made that the user is within the certain distance of the user input device, and in response, the emission of UV light is prevented.

According to yet another aspect, a self-sterilizing user input device includes a housing, a touchscreen, a backlight, a UV light source, and a controller. The touchscreen is positioned within a front aperture of the housing for receiving tactile input from a user. The backlight is positioned between a rear surface of the housing and the touchscreen, and is used to illuminate the touchscreen from behind. The UV light source is positioned with the backlight and emits UV light onto the touchscreen from behind at a sterilization wavelength. The controller selectively activates and deactivates the UV light source according to whether or not the user is present at the user input device.

It should be appreciated that the above-described subject matter may also be implemented as a computer-controlled apparatus, a computer process, a computing system, or as an article of manufacture such as a computer-readable medium.

These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 7 shows an illustrative computer architecture for a self-sterilizing user input device.

DETAILED DESCRIPTION

Figure 1:
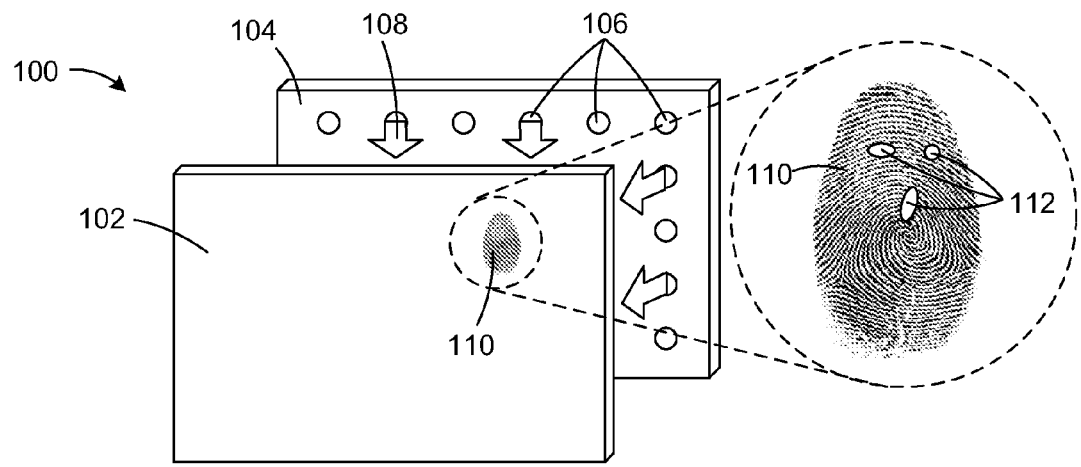
FIG. 1 is a partially exploded perspective view of a conventional user input device showing a conventional touchscreen and backlight with light emitting diodes (LEDs)

The following detailed description is directed to technologies for sterilizing a touchscreen of a user input device. As discussed briefly above, the touchscreens and other tactile input mechanisms of kiosks, ATMs, smart phones, gaming systems, and computers are breeding grounds for bacteria and other organisms that are easily transferred from person to person as often hundreds or even thousands of people use the devices on a daily or weekly basis. While user input devices such as these are often cleaned and disinfected utilizing common liquid agents, the infrequency of the cleanings coupled with the vast number of people using the devices promotes the spread of disease. Although UV light has been used for sterilization purposes in the medical field, existing UV purifiers are configured as separate, stand-alone sterilization devices and have not been used in common cleaning applications or environments.

Aspects of the disclosure provided herein allow for the incorporation of UV light sources within user input devices to regularly clean and disinfect touchscreens, displays, or other associated input mechanisms continuously as the devices are being used. Throughout this disclosure, "user input devices" may include any device having a touchscreen, buttons, stylus, pen, or any other input mechanism that a user would touch during interaction. While the various embodiments described herein may be described in the context of a touchscreen that receives user input via direct user contact on a display screen such as a liquid crystal display (LCD), it should be appreciated that the concepts described herein may be utilized in any application in which a UV light source may be incorporated into a user device and activated to emit UV light onto a surface or object that may receive tactile contact from a user.

As will be described in detail below, aspects of the disclosure provide safety measures that allow for the selective application of UV light. According to various aspects, the UV light source is activated and deactivated according to various criteria that may be used to indicate whether or not a person is using, or is at or within proximity of, the user input device. In the following detailed description, references are made to the accompanying drawings that form a part hereof, and which are shown by way of illustration specific embodiments or examples. Referring now to the drawings, in which like numerals represent like elements through the several figures, aspects of a system and methodology for sterilizing user input devices will be described.

Turning now to FIG. 1, a conventional LED backlit device 100 will be described. The conventional LED backlit device 100 includes a touchscreen 102 and a conventional backlight 104. The touchscreen 102 may include an LCD display or any other type of display that is configured to receive tactile input from a user, including but not limited to cathode ray tube and plasma displays. The touchscreen 102 is commonly illuminated via a backlight source 104. One commonly used backlight source 104 includes an LED matrix having any number of LEDs 106. The LEDs 106 emit light 108 onto a rear surface of the touchscreen 102 to illuminate the displayed subject matter. Conventionally, the LEDs 106 may include white LEDs, or blue LEDs with yellow phosphor to simulate white light. Alternatively, as will be shown in FIG. 2 below, the LEDs 106 may include red, green, and blue (RGB) LEDs to enhance the color characteristics of the touchscreen 102.

As seen from the enlarged view in FIG. 1, tactile input 110 from a user onto the touchscreen 102 of the conventional LED backlit device 100 can leave bacteria 112 or other microorganisms that can be transferred to another user when he or she contacts the touchscreen 102 in the same location. This occurs frequently on touchscreens 102 of ATMs or other kiosks that provide number pads or other specific input locations that are repeatedly touched by subsequent users. It should be understood that the illustrations of the various user input devices have been simplified to show only the components that may be applicable to this disclosure. Any number and type of additional components, such as filters and light valves, may be used in conjunction with the user input devices shown and described herein.

Figure 2:
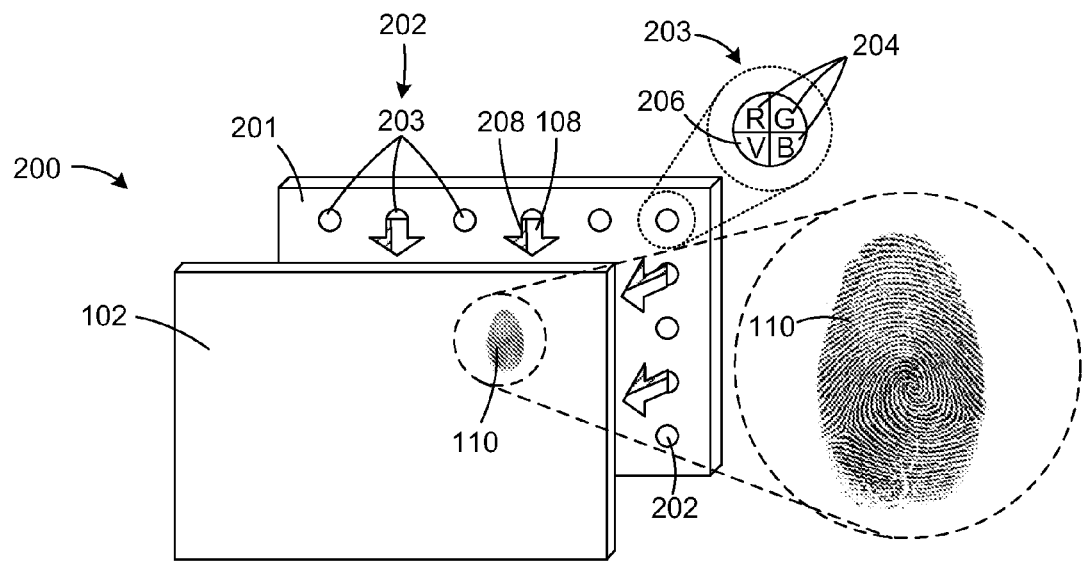
FIG. 2 is a partially exploded perspective view of a self-sterilizing user input device showing a touchscreen and backlight with UV LEDs for sterilizing the touchscreen according to various embodiments presented herein.

FIG. 2 shows a self-sterilizing user input device 200 that includes a touchscreen 102 and a backlight 201. According to this embodiment, the backlight 201 includes an LED matrix having any number of LEDs 203. As seen in the enlarged view of an LED 203, the LEDs 203 are configured not only as a conventional light source, but are also configured as a UV light source 202. The enlarged view of the LED 203 shows that the LED 203 may include conventional RGB LEDs 204 and one or more UV LEDs 206.

While the conventional RGB LEDs 204 provide the light 108 for the conventional backlighting functionality of the backlight 201, the UV LEDs 206 are configured as the UV light source 202 to provide UV light 208 at sterilization wavelengths that are optimal for disinfection of the touchscreen 102. According to one implementation, the sterilization wavelengths include a germicidal wavelength of approximately 254 nm, although any wavelength suitable for eliminating or diminishing bacteria on the surface of the touchscreen 102 may be used. As will be described in greater detail below, the sterilization wavelengths may be variable so that the self-sterilizing user input device 200 may alter the wavelength according to user presence or other factors to maximize the effectiveness of the touchscreen 102 sterilization.

It should be appreciated that the precise number and placement of UV LEDs 206 used for sterilization may depend on the specific application of the self-sterilizing user input device 200, such as the size of the touchscreen 102 and the desired pattern and intensity of the UV light 208. As can be seen in the enlarged view of the location of the tactile input 110, the bacteria 112 deposited on the touchscreen 102 of the conventional LED backlit device 100 is not present on the self-sterilizing user input device 200 as a result of the UV light 208 emitted by the UV LEDs 206.

Figure 3:
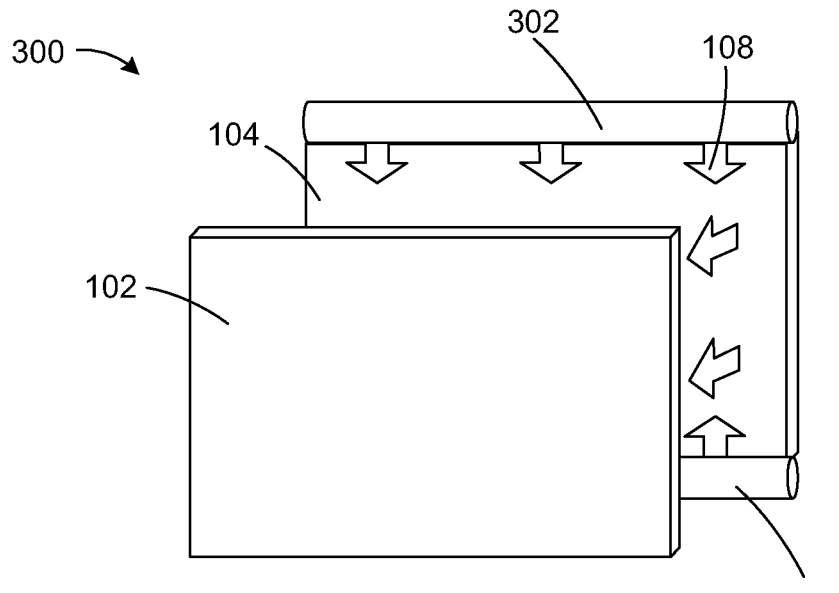
FIG. 3 is a partially exploded perspective view of a conventional user input device showing a conventional touchscreen and cold cathode fluorescent lamp (CCFL) backlight.

FIG. 3 shows a conventional CCFL backlit device 300. Similar to the conventional LED backlit device 100 shown and described above, a conventional backlight 104 is used to illuminate a touchscreen 102 from a rear side of the display. However, rather than utilizing LEDs 106 to provide illumination, the backlight 104 utilizes CCFLs 302 to provide the light 108 for the touchscreen 102. The self-sterilization concepts and technologies described herein can be applied to CCFL backlight 104 configurations, as shown in FIG. 4.

Figure 4:
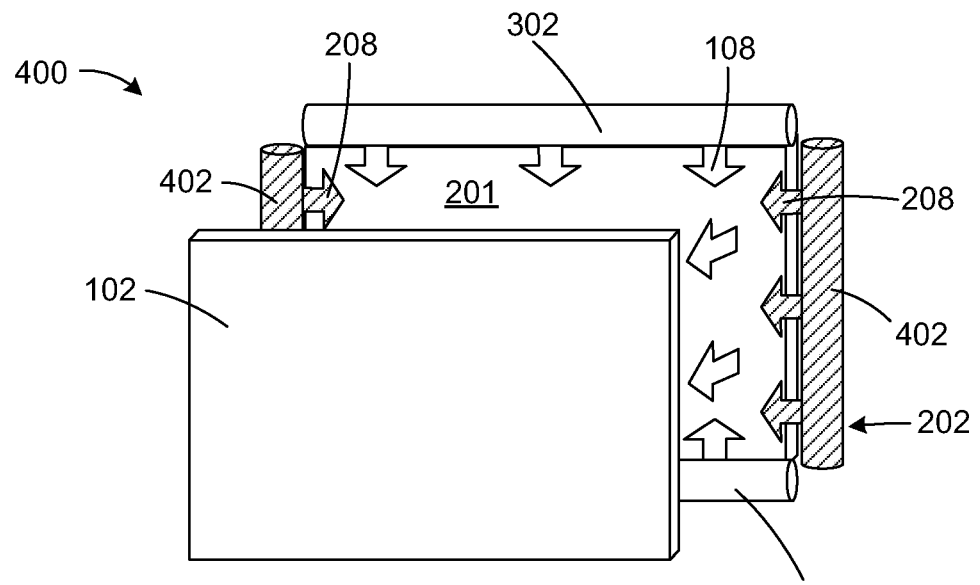
FIG. 4 is a partially exploded perspective view of a self-sterilizing user input device showing a touchscreen and CCFL backlight with UV fluorescent lamps for sterilizing the touchscreen according to various embodiments presented herein.

FIG. 4 depicts a self-sterilizing user input device 400, which incorporates a UV light source 202, configured as UV fluorescent lamps 402, into the backlight 201 with the conventional CCFLs 302. The UV fluorescent lamps 402 ionize mercury vapor to produce UV radiation. The resulting UV light 208 may be selectively produced to disinfect the touchscreen 102 in the absence of a user, ensuring the safe sterilization of the user input device 400. While two UV fluorescent lamps 402 are shown as being positioned on opposing sides of the backlight 201 and touchscreen 102, any number of UV fluorescent lamps 402 may be used at any desired positions within the self-sterilizing user input device 400 suitable for emitting the UV light 208 onto the touchscreen 102 at a desired pattern and intensity. Moreover, it should be appreciated that the UV fluorescent lamps 402 may be configured to emit light in the visible spectrum as well as UV light 208. In doing so, the UV fluorescent lamps 402 may include one or more UV lamps and conventional lamps within a common housing, or may utilizing a single lamp that selectively emits light 108 or UV light 208 utilizing one or more light filters (not shown).

While the various embodiments disclosed herein are described in the context of LEDs 106 and CCFLs 302 used as the backlights 104, with corresponding UV LEDs 206 and UV fluorescent lamps 402 as UV light sources 202, it should be understood that the concepts presented herein are not limited to these backlight and UV light source configurations. Rather, any type of UV light source 202 configured to provide UV light 208 onto the touchscreen 102 may be utilized with any conventional backlight 104 configuration, or with a user input device that relies on front lighting rather than a conventional backlight 104.

Figure 5:
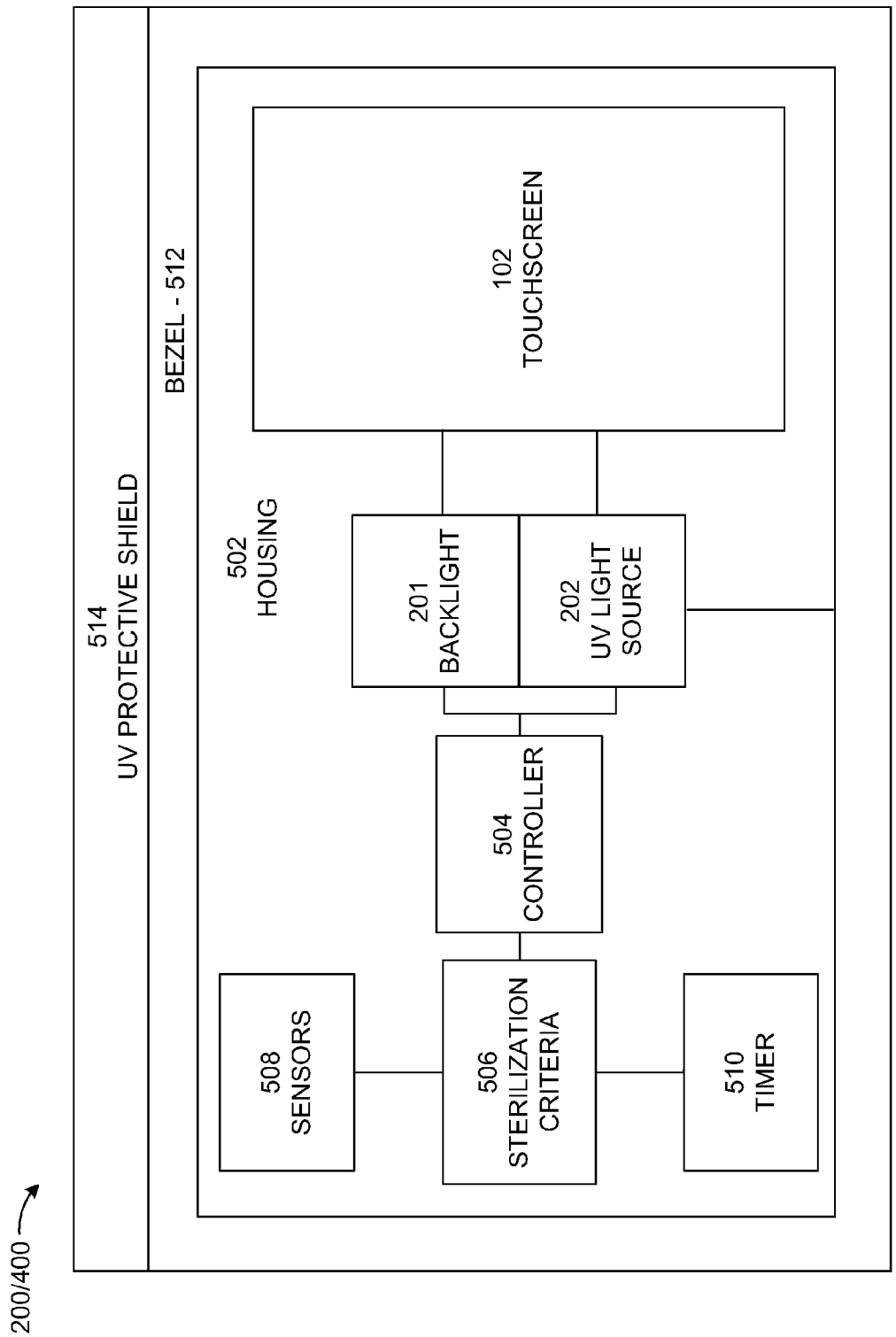
FIG. 5 is an illustrative block diagram showing various components of a user input device according to various embodiments presented herein.

FIG. 5 shows a simplified block diagram of a self-sterilizing user input device (200, 400) according to various embodiments described herein. It should be appreciated that applications of the self-sterilizing user input device (200, 400) are not limited to the components shown in FIG. 5, and may conversely not include all of the components shown. For example, as will be described in further detail below, the UV protective shield 514, the bezel 512, and the sensors 508 may or may not be present in the self-sterilizing user input device (200, 400) according to the particular implementation.

According to various embodiments described herein, the self-sterilizing user input device (200, 400) may include a touchscreen 102, a backlight 201, and a UV light source 202 as discussed above. A housing 502 may encompass these components such that the backlight 201 is positioned proximate to a rear surface of the housing, while the touchscreen is mounted within a front aperture of the housing. It should be appreciated that the UV light source (202) may be incorporated into the backlight 201, or may be separate from, but used in conjunction with, a conventional backlight 104. Alternatively, the UV light source 202 may be positioned inside the housing 502 and behind the touchscreen 102, without utilizing a backlight 201. According to another alternative configuration, the housing 502 may include a bezel 512 around a front aperture in which the touchscreen 102 is mounted. The UV light source 202 may be installed within the bezel 512 such that the UV light 208 is emitted onto the front surface of the touchscreen 102 rather than through the rear surface. As with the embodiments described above, when the UV light source 202 is incorporated into the bezel 512, the UV light source 202 may include UV LEDs 206, UV fluorescent lamps 402, or any other type or combination of suitable UV light sources 202.

One consideration to be made when sterilizing the touchscreen 102 with UV light 208 is safety. UV radiation can be dangerous to people if there is prolonged exposure to skin, leading to sunburn and potentially skin cancer, as well as potential damage to the eyes if exposed to the radiation. For this reason, the self-sterilizing user input device (200, 400) includes safety aspects that selectively activate and deactivate the UV light source 202 according to the presence or absence of a user of the device. As will be described in greater detail below, the self-sterilizing user input device (200, 400) may also be configured to modify or modulate the intensity or wavelength of the UV light 208 according to any number and type of sterilization criteria 506. According to various embodiments, a user's presence at or near the self-sterilizing user input device (200, 400) can be determined in various ways, which will be described below.

A controller 504 is connected to the UV light source 202 and may be used to detect the presence of a person at or within a predetermined proximity to the self-sterilizing user input device (200, 400), and to control the emissions of UV light 208 accordingly. It should be understood that the term "controller" is used herein to generically refer to any hardware and/or software, such as a processor or microcontroller, capable of executing stored computer-readable instructions to perform the user presence determinations and corresponding UV light emission control functionality described herein. The controller 504 may utilize any quantity and type of sterilization criteria 506 to determine whether a person is within a predetermined proximity to the self-sterilizing user input device (200, 400). Examples of sterilization criteria 506 may include, but are not limited to, proximity of a user to the self-sterilizing user input device (200, 400), time of day, and the status of a UV protective shield 514, which will be described further below. The proximity of a user to the device may be determined using data from any number and type of sensors 508 and time data from a timer 510 or clock.

According to one embodiment, the sensors 508 may include proximity sensors 508 and/or motion sensors 508. For example, using one or more proximity sensors 508 positioned within a predetermined perimeter of the self-sterilizing user input device (200, 400), the controller 504 may receive an indication that a person, animal, or object has entered the predetermined perimeter. Consequently, the controller 504 determines that a potentially unsafe environment exists for UV light 208 emissions and deactivates the UV light source 202 if currently activated, or prevents the activation of the UV light source 202 if currently not activated. Once the proximity sensors indicate that the person, animal, or object has exited the predetermined perimeter, then the controller 504 may again activate the UV light source 202 or allow the activation of the UV light source 202 according to stored sterilization rules or instructions.

Similarly, the sensors 508 may include motion sensors so that the controller 504 receives an indication of movement within a predefined perimeter around the self-sterilizing user input device (200, 400) and determines that a person is present, subsequently deactivating the UV light source 202 or preventing the activation of the UV light source 202. When the motion sensors 508 detect a lack of movement or no movement for a predetermined amount of time, the controller may activate the UV light source 202 to sterilize the touchscreen 102.

According to another implementation, the controller 504 may determine that a user is present when user input is received on the touchscreen 102. When tactile input 110 is detected, the controller 504 ensures that the UV light source 202 is deactivated. Conversely, when user input has not been detected for a predetermined quantity of time, then the controller 504 may determine that a person is not present and activate the UV light source 202 to disinfect the touchscreen 102. It should be appreciated that the user presence determinations and the specific factors used by the controller 504 in making these determinations (i.e., predetermined quantities of time since tactile input received, or since a proximity or motion sensor 508 is triggered) may be stored in the self-sterilizing user input device (200, 400) as sterilization rules or instructions.

According to yet another implementation, the activation of the UV light source 202 may be determined according to a time of day. For example, an ATM inside of a bank may be programmed to activate the UV light source 202 during hours in which the bank is closed to the public, ensuring adequate sterilization at least before and after banking hours, while minimizing or eliminating potential exposure of UV light 208 to the public. Alternatively, as mentioned above, the sterilization rules may instruct the controller 504 to vary the wavelength or other characteristics of the UV light 208 according to any number and type of sterilization criteria 506. For example, the intensity or wavelength of the UV light 208 may be minimized during periods of frequent use, as detected by the sensors 508. However, during periods of decreased usage, the controller 504 may increase the intensity or wavelength of the UV light 208 by altering the power input of the UV light source 202.

As an alternative safety measure, embodiments of the self-sterilizing user input device (200, 400) may utilize a UV protective shield 514 to protect users from UV radiation exposure. The UV protective shield 514 may be a physical cover for the touchscreen 102 that includes UV impermeable material to block UV radiation from escaping. Although the UV protective shield 514 is shown in the diagram of FIG. 5 as a block at the top of the self-sterilizing user input device (200, 400), it should be appreciated that it may be a cover that is sized to encompass the front surface of the housing, and may be hinged such that it rotates around any edge of the front surface of the housing to close over the touchscreen 102. The UV protective shield 514 may be connected to an actuation system that is controlled by the controller 504 such that the UV protective shield 514 is mechanically shuttered at predetermined times for sterilization.

Upon determining that a person is not at or near the self-sterilizing user input device (200, 400) using any of the methods described above, the controller 504 may close the UV protective shield 514 and activate the UV light source 202 to sterilize the touchscreen. Alternatively, because the UV protective shield 514 is configured to physically close over the touchscreen 102 and block all UV light 208 emanating from the UB light source 202, the controller 504 may activate the shield and UV light source 202 at predetermined time intervals, irrespective of the presence of a person at or near the self-sterilizing user input device (200, 400). As an example, after each ATM use, the controller 504 may activate the UV protective shield 504, such as closing a cover or shutters over the display, for a minimal amount of time while the UV light source 202 is activated. After sterilization, the UV protective shield 504 is deactivated and the sterilized ATM display is ready for the next customer.

The UV protective shield 514 may alternatively be a UV filter positioned between the UV light source 202 and a user, either behind or in front of the touchscreen 102. The UV filter may be configurable such that it can be activated by the controller 504 to block UV light 208, and deactivated by the controller 504 to allow UV light 208 to pass through the UV filter. In this manner, the controller 504 may activate the UV filter when it is determined that a person is within a predetermined proximity to the self-sterilizing user input device (200, 400).

Figure 6:
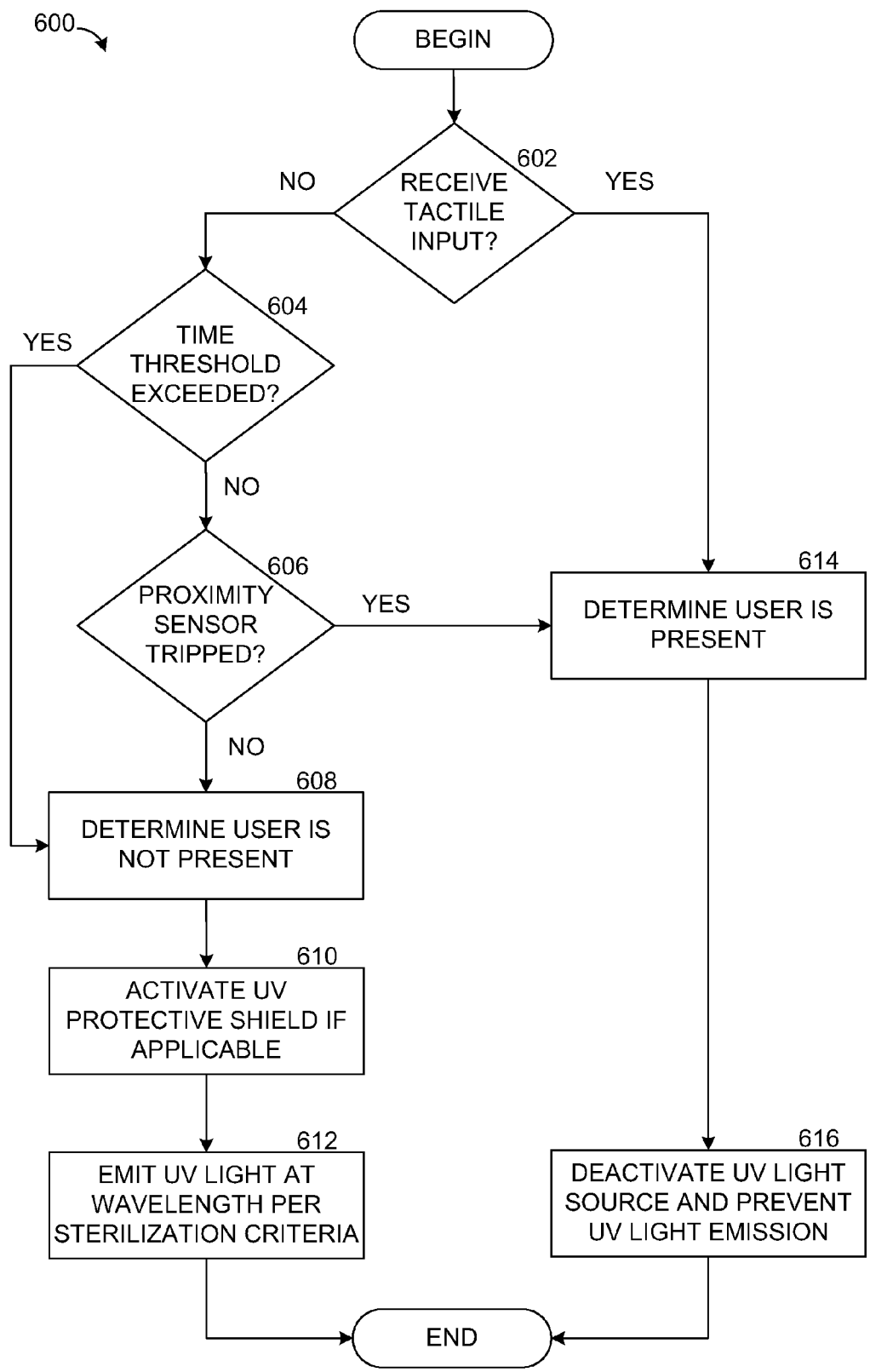
FIG. 6 is a flow diagram showing an illustrative process for sterilizing a user input device according to various embodiments presented herein.

Referring now to FIG. 6, additional details will be provided regarding the embodiments presented herein for sterilizing a touchscreen 102 of a user input device according to the disclosure provided herein. It should be appreciated that the logical operations described with respect to the flow diagram are implemented (1) as a sequence of computer implemented acts or program modules running on a computing system, or self-sterilizing user input device (200, 400), and/or (2) as interconnected machine logic circuits or circuit modules within the self-sterilizing user input device (200, 400). The implementation is a matter of choice dependent on the performance and other characteristics of the device.

Accordingly, the logical operations described with respect to the various flow diagrams herein are referred to variously as states operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

The routine 600 begins at operation 602, where a determination is made by the controller 504 as to whether tactile input 110 has been received at the touchscreen of the self-sterilizing user input device (200, 400). If tactile input 110 has been received, then the routine proceeds to operation 614, where it is determined that a user is present at or near the self-sterilizing user input device (200, 400), and the UV light source 202 is deactivated and UV light 208 emission is prevented at operation 616. However, if at operation 602, tactile input 110 has not been received, then the operation proceeds to operation 604, where the controller 504 determines if a time threshold has been exceeded. As described above, a timer 510 may be utilized according to sterilization rules to determined the length of time since the last tactile input 110 was received or the length of time since a proximity or motion sensor 508 detected a user's presence. If the threshold length of time has been exceeded, then the routine 600 proceeds to operation 608, where the controller 508 determines that a user is not at or near the self-sterilizing user input device (200, 400).

However, if at operation 604, it is determined that a threshold time has not been exceeded, then the routine 600 continues to operation 606, where a determination is made as to whether a proximity or motion sensor 508 has been tripped. In other words, it is determined if a proximity sensor 508 or motion sensor 508 has detected movement near the self-sterilizing user input device (200, 400) or within a perimeter of the self-sterilizing user input device (200, 400). If so, then the routine proceeds to operation 614, where it is determined that a user is present at or near the self-sterilizing user input device (200, 400), and the UV light source 202 is deactivated and UV light 208 emission is prevented at operation 616. However, if at operation 606, it is determined that a sensor 508 has not been tripped, then the routine continues to operation 608, and it is determined that a user is not present at or near the self-sterilizing user input device (200, 400).

After determining that a user is not present, the controller 504 may activate the UV protective shield 514, if the self-sterilizing user input device (200, 400) is configured with this feature. At operation 612, the controller 504 activates the UV light source 202, which emits UV light 208 onto the touchscreen 102 at a desired wavelength according to sterilization criteria 506 or rules, and the routine 600 ends.

FIG. 7 shows an illustrative computer architecture for a self-sterilizing user input device (200, 400) capable of executing the software components described herein for sterilizing a touchscreen 102 utilizing a UV light source 202 in the manner presented above. The computer architecture shown in FIG. 7 illustrates a conventional desktop, laptop, or server computer and may be utilized to execute any aspects of the software components presented herein.

The computer architecture shown in FIG. 7 includes a central processing unit 702 (CPU), which may be the controller 504, a system memory 708, including a random access memory 714 (RAM) and a read-only memory (ROM) 716, and a system bus 704 that couples the memory to the CPU 702. A basic input/output system containing the basic routines that help to transfer information between elements within the self-sterilizing user input device (200, 400), such as during startup, is stored in the ROM 716. The self-sterilizing user input device (200, 400) further includes a mass storage device 710 for storing an operating system 718, application programs, and other program modules, which are described in greater detail herein.

The mass storage device 710 is connected to the CPU 702 through a mass storage controller (not shown) connected to the bus 704. The mass storage device 710 and its associated computer-readable media provide non-volatile storage for the self-sterilizing user input device (200, 400). Although the description of computer-readable media contained herein refers to a mass storage device, such as a hard disk or CD-ROM drive, it should be appreciated by those skilled in the art that computer-readable media can be any available computer storage media that can be accessed by the self-sterilizing user input device (200, 400).

By way of example, and not limitation, computer-readable media may include volatile and non-volatile, removable and non-removable media implemented in any method or technology for storage of information such as computer-readable instructions, data structures, program modules or other data. For example, computer-readable media includes, but is not limited to, RAM, ROM, EPROM, EEPROM, flash memory or other solid state memory technology, CD-ROM, digital versatile disks (DVD), HD-DVD, BLU-RAY, or other optical storage, magnetic cassettes, magnetic tape, magnetic disk storage or other magnetic storage devices, or any other medium which can be used to store the desired information and which can be accessed by the self-sterilizing user input device (200, 400).

According to various embodiments, the self-sterilizing user input device (200, 400) may operate in a networked environment using logical connections to remote computers through a network such as the network 720. The self-sterilizing user input device (200, 400) may connect to the network 720 through a network interface unit 706 connected to the bus 704. It should be appreciated that the network interface unit 706 may also be utilized to connect to other types of networks and remote computer systems. The self-sterilizing user input device (200, 400) also includes a touchscreen 102 for receiving and processing tactile input and displaying information.

As mentioned briefly above, a number of program modules and data files may be stored in the mass storage device 710 and RAM 714 of the self-sterilizing user input device (200, 400), including an operating system 718 suitable for controlling the operation of a networked desktop, laptop, or server computer. The mass storage device 710 and RAM 714 may also store one or more program modules. In particular, the mass storage device 710 and the RAM 714 may store the sterilization criteria 506 and the sterilization rule 724, as well as a sterilization application 722 operative to execute the sterilization rules 724. The mass storage device 710 and the RAM 714 may also store other types of program modules.

Based on the foregoing, it should be appreciated that technologies for sterilizing a touchscreen 102 of a self-sterilizing user input device (200, 400) are provided herein. Utilizing the concepts disclosed above, the spread of contagious disease caused by repeated contact of a user input device by numerous people can be controlled via sterilization of the contact surfaces utilizing a UV light source 202 that is built into the device. Safe sterilization is ensured through intelligent, selective application of UV light 208 according to the presence or absence of people at or around the self-sterilizing user input device (200, 400).

Although the subject matter presented herein has been at least partially described in language specific to computer structural features and methodological acts, it is to be understood that the disclosure defined in the appended claims is not necessarily limited to the specific features, acts, or media described herein. Rather, the specific features, acts and mediums are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the present disclosure, which is set forth in the following claims.

What is claimed is:

1. A self-sterilizing user input device, comprising:
a touchscreen configured to receive tactile user input and to provide a first output signal indicative of tactile user input;
a timer, functionally connected to the touchscreen and responsive to the first output signal to provide a second output signal if the first output signal does not indicate tactile user input for a predetermined period of time;
a proximity sensor responsive to presence of a user within a predetermined proximity to provide a third output signal indicative of user presence;
an ultraviolet (UV) light source configured to emit UV light onto the touchscreen at a sterilization wavelength; and
a controller, functionally connected to the touchscreen, the timer, the proximity sensor, and the UV light source, and configured to activate the UV light source if both the second output signal indicates no tactile user input for at least the predetermined period of time and the third output signal indicates no user presence, and to deactivate the UV light source if either the second output signal indicates tactile user input or the third output signal indicates user presence.

2. The self-sterilizing user input device of claim 1, further comprising a backlight configured to illuminate the touchscreen.

3. The self-sterilizing user input device of claim 2, wherein the backlight comprises a plurality of light-emitting diodes (LEDs), and wherein the UV light source comprises a plurality of UV LEDs positioned among the plurality of LEDs such that the UV light is emitted on the touchscreen from behind the touchscreen when the plurality of UV LEDs are activated by the controller.

4. The self-sterilizing user input device of claim 2, wherein the backlight comprises a cold cathode fluorescent lamp (CCFL), and wherein the UV light source comprises a UV fluorescent lamp such that the UV light is emitted on the touchscreen from behind the touchscreen when the UV fluorescent lamp is activated by the controller.

5. The self-sterilizing user input device of claim 1, further comprising a housing encompassing the touchscreen and the controller.

6. The self-sterilizing user input device of claim 5, wherein the UV light source is disposed within the housing such that the UV light is output on the touchscreen from behind the touchscreen when the UV light source is activated by the controller.

7. The self-sterilizing user input device of claim 5, wherein the UV light source is externally attached to the housing such that the UV light is output on the touchscreen from in front of the touchscreen when the UV light source is activated by the controller.

8. The self-sterilizing user input device of claim 7, wherein the housing comprises a bezel surrounding the touchscreen, and wherein the UV light source is disposed within the bezel of the housing.

9. The self-sterilizing user input device of claim 1, wherein the controller being operative to selectively activate and deactivate the UV light source according to user presence comprises the controller being operative to detect a user absence according to a timer and a proximity sensor and to activate the UV light source at a predetermined time since detecting an absence of a user within a predetermined proximity of the user input device.

10. The self-sterilizing user input device of claim 1, further comprising a UV protective shield, wherein the controller is further configured to activate the UV protective shield upon activation of the UV light source.

11. The self-sterilizing user input device of claim 1, wherein the controller is further configured to vary the sterilization wavelength according to at least one predefined sterilization criteria.

12. The self-sterilizing user input device of claim 11, wherein the at least one predefined sterilization criteria comprises time of day, status of a UV protective shield, or proximity of a user to the user input device.

13. A self-sterilizing user input device, comprising:
a housing;

a touchscreen positioned within a front aperture of the housing and configured to receive tactile user input and to provide a first output signal indicative of tactile user input;

a timer, functionally connected to the touchscreen and responsive to the first output signal to provide a second output signal if the first output signal does not indicate tactile user input for a predetermined period of time;

a proximity sensor responsive to presence of a user within a predetermined proximity to provide a third output signal indicative of user presence;

a backlight positioned between a rear surface of the housing and the touchscreen, the backlight configured to illuminate the touchscreen;

a UV light source positioned proximate to the backlight between the rear surface of the housing and the touchscreen, the UV light source configured to emit UV light onto the touchscreen at a sterilization wavelength from a rear side of the touchscreen; and a controller, positioned within the housing and functionally connected to the touchscreen, the timer, the proximity sensor, and the UV light source, and configured to activate the UV light source if both the second output signal indicates no tactile user input for at least the predetermined period of time and the third output signal indicates no user presence, and to deactivate the UV light source if either the second output signal indicates tactile user input or the third output signal indicates user presence.

* * * * *